United States Patent [19]

Hall, deceased et al.

[11] Patent Number: 4,992,545

[45] Date of Patent: Feb. 12, 1991

[54] PROCESS FOR PREPARING 4-SUBSTITUTED AZETIDINONES

[75] Inventors: David A. Hall, deceased, Late of Indianapolis, Ind., by Lillian C. Hall, personal representative; John M. Morin, Jr., Brownsburg; Robert J. Ternansky, Noblesville, both of Ind.;

[73] Assignee: Eli Lilly and Company, Indianapolis, Ind.

[21] Appl. No.: 410,173

[22] Filed: Sep. 20, 1989

[51] Int. Cl.$^5$ ............ C07D 205/095; C07D 205/085; C07B 37/04; C07B 37/06

[52] U.S. Cl. .................. 540/359; 204/59 R; 540/200; 540/362; 540/363; 540/364

[58] Field of Search ............ 540/200, 363, 364, 359, 540/362

[56] References Cited

U.S. PATENT DOCUMENTS

| | | | |
|---|---|---|---|
| 4,230,619 | 10/1980 | Foglio | 540/357 |
| 4,421,686 | 12/1983 | Mueller | 540/359 |
| 4,559,406 | 12/1985 | Lempert | 540/200 |
| 4,588,484 | 5/1986 | Justice et al. | 204/59 |
| 4,652,651 | 3/1987 | Furlenmeier | 548/194 |
| 4,665,171 | 5/1987 | Evans et al. | 540/364 |
| 4,683,303 | 7/1987 | Pfaendler | 540/362 |
| 4,771,135 | 9/1988 | Blaszczak | 450/360 |

OTHER PUBLICATIONS

Hans Rudolf Pfaendler et al., Heterocycles, vol. 23, No. 2, 1985, pp. 265–272.
Dabby et al., Battersea Polytechnic, London, S.W.11., 1952, pp. 4881–4882.
Bodurow et al., Tetrahedron Letters, vol. 30, No. 18, pp. 2321–2324, 1989.
*Tetrahedron Letters*, Posner et al., No. 12, pp. 935–938, 1973.
*J. Org. Chem.*, Posner et al., vol. 38, No. 16, 1973 pp. 2747–2756.
*J. Am. Chem. Soc.*, 79, 5279 (1957), N. J. Leonard and F. R. Hauck.

Primary Examiner—Mark L. Berch
Attorney, Agent, or Firm—James J. Sales; Leroy Whitaker

[57] ABSTRACT

A process for preparing 3-4-cis-$\beta,\beta$-(4)-substituted and 3-4-trans,$\beta,\alpha$- (4)-substituted azetidinones is provided. Also provided are novel 4,4-disubstituted azetidinones.

19 Claims, No Drawings

PROCESS FOR PREPARING 4-SUBSTITUTED AZETIDINONES

BACKGROUND OF THE INVENTION

This invention relates to β-lactam antibiotics. In particular, it relates to a process for preparing certain 4-substituted azetidinones, primarily useful as intermediates to β-lactam antibiotics.

Among the newer β-lactam antibiotics currently under investigation are the 1-carba(1-dethia)-3-cephem-4-carboxylic acids. These β-lactam compounds provide significant synthetic challenges. One of the more noteworthy approaches to total synthesis of 1-carba(1-dethia)-3-cephem-4-carboxylic acids is the asymmetric route described by Evans, et al., U.S. Pat. No. 4,665,171.

One further route to cis-chiral azetidinones with readily derivatized 4-allyl (and substituted allyl) groups, is provided by Blaszczak, U.S. Pat. No. 4,771,134. The Blaszczak method utilizes a 4-acetoxy azetidinone as starting material to provide 4-(substituted selenyl)azetidinones. The 4-(substituted selenyl)azetidinones are converted to 4-allyl(and substituted allyl)azetidinones under free radical conditions using a (2-substituted or unsubstituted) allyl tin reagent.

SUMMARY OF THE INVENTION

A process for preparing cis,β,β(and trans β,α)-3-protected amino-4-alkyl azetidinones is provided via alkylation of trans,β,α-3-protected amino-4-phenylsulfonyl azetidinones followed by reductive elimination of the phenylsulfonyl moiety.

As an example of the present invention, 3-β-phenoxyacetyl-amino-1t-butyldimethylsilyl-4-α-phenyl sulfonyl-azetidin-2-one is treated with n-butyllithium and 1-bromo-4-butene to provide 3-β-phenoxyacetylamino-1-t-butyldimethylsilyl-3-α-phenylsulfonyl-3-β-1-butene-4-yl-azetidin-2-one. The 4-disubstituted intermediate can then be readily converted to the corresponding 4-butenyl derivative by treatment with a hydride reducing agent, such as lithium tri-tert-butoxyaluminohydride, or by electrolytic reduction, or by dissolving metal reduction.

DETAILED DESCRIPTION OF THE INVENTION

The present invention provides a process for preparing compounds of Formula (I):

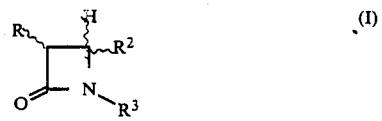

wherein R is a protected amino group; hydroxy($C_1$-$C_4$)alkyl, protected hydroxy($C_1$-$C_4$)alkyl hydrogen; $C_2$-$C_4$ alkenyl; $C_1$-$C_4$ alkyl or hydrogen; $R^2$ is $C_1$-$C_{12}$ alkyl, $C_1$-$C_{12}$ substituted alkyl, $C_2$-$C_6$ alkenyl, $C_2$-$C_6$ substituted alkenyl, $C_2$-$C_6$ alkynyl, $C_2$-$C_6$ substituted alkynyl; and $R^3$ is an amide-protecting group, $C_1C_6$ alkyl, $C_1C_6$ substituted alkyl, $C_2C_6$ alkenyl, $C_2C_6$ alkynyl, or hydrogen; which comprises:

(a) reaction of a compound of Formula (II):

wherein $R^1$ is triphenylphosphonium, —$SO_2R'$, CN, —$SiR'_3$,

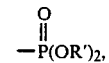

or —$CO_2R'$ wherein $R'$ is $C_1$-$C_6$ alkyl, phenyl, substituted phenyl, phenyl $C_1$-$C_6$ alkyl, or $C_1$-$C_6$ substituted alkyl, with strong base in the presence of a compound of the formula $R^2$—L, wherein L is a leaving group; followed by (b) reduction with a hydride reducing agent, reduction under dissolving metal conditions or reduction under electrolytic reduction conditions.

As further aspects of the present invention, there are provided the individual processes (a) and (b), above In the above formulae, the undulating lines emanating from the 3- and 4-positions of the β-lactam ring denote the α and β configurations, as well as compounds wherein there is a mixture of α- and β-isomers.

In the above formulae, the term "$C_1$-$C_{12}$ alkyl" denotes such radicals as methyl, ethyl, n-propyl, iso-propyl, n-butyl, sec-butyl, tert-butyl, amyl, tert-amyl, hexyl, dodecyl, lauryl and the like. The preferred "$C_1$-$C_{12}$ alkyl" groups are methyl, and t-butyl.

The term "$C_1$-$C_{12}$ substituted alkyl" denotes the above $C_1$-$C_{12}$ alkyl groups that are substituted by one or two halogen, hydroxy, protected hydroxy, amino, protected amino, $C_1$-$C_7$ acyloxy, nitro, carboxy, protected carboxy, carbamoyl, carbamoyloxy, cyano, methylsulfonylamino or $C_1$-$C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, methoxyethyl, ethoxymethyl, t-butoxymethyl, acetoxymethyl, 2-amino(iso-propyl), 2-carbamoyloxyethyl, and the like. A preferred group of examples within the above "$C_1$-$C_{12}$ substituted alkyl" group includes the substituted methyl group, in other words, a methyl group substituted by the same substituents as the "$C_1$-$C_{12}$ substituted alkyl" group. One of ordinary skill will appreciate that there exist groups within the above definition as well as other groups defining $R^2$ which could be incompatible for use with a strong base and, of course, such groups are excluded from the definition herein.

The term "$C_2$-$C_6$ alkenyl" denotes groups possessing between two and six carbon atoms and at least one double carbon-carbon bond. A few examples of such groups are vinyl, 1-propene-2-yl, 1-butene-4-yl, 1- pentene-5-yl, 1-hexene-6-yl, 1-propene-1-yl, 1-butene-1-yl, 1-pentene-1-yl, 1-hexene-1-yl, and like groups.

The term "$C_2$-$C_6$ substituted alkenyl" denotes the above $C_2$-$C_6$ alkenyl groups that are substituted by one or more halogen, hydroxy, protected hydroxy, protected amino, $C_1$-$C_7$ acyloxy, nitro, carboxy, protected carboxy, carbamoyl, carbamoyloxy, cyano, methylsulfonylamino or $C_1$-$C_4$alkoxy groups. The $C_2$-$C_6$substituted alkenyl groups may be substituted once or twice with the same or with different substituents.

The term "$C_2$-$C_6$alkynyl" denotes groups possessing between two and six carbon atoms and at least one triple carbon-carbon bond. A few examples of such groups include ethynyl, 1-propyne-2-yl, 1-butyne-4-yl, 1-pentyne-5-yl, 1-butyne-1-yl, and like groups.

The term "$C_2$-$C_6$ substituted alkynyl" denotes the above $C_2$-$C_6$alkynyl groups that are substituted by one or more halogen, hydroxy, protected hydroxy, protected amino, $C_1$-$C_7$acyloxy, nitro, carboxy, protected carboxy, carbamoyl, carbamoyloxy, cyano, methylsulfonylamino, or $C_1$-$C_4$alkoxy groups. The $C_2$-$C_6$substituted alkynyl groups may be substituted once or twice with the same or different substituents.

The term "substituted phenyl" denotes a phenyl ring substituted with one or more halogen, hydroxy, protected hydroxy, protected amino, $C_1$-$C_7$acyloxy, nitro, cyano, methylsulfonylamino, or $C_1$-$C_4$alkoxy groups. The phenyl ring may be substituted one or more times with the same or different substituents.

In the above process, the term "protected amino group" refers to an amino group substituted by groups commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl, iodoacetyl, phenoxyacetyl and phenylacetyl groups, urethane-type blocking groups such as benzyloxycarbonyl, allyloxycarbonyl 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1yloxycarbonyl, 1,1-diphenylprop-1-yloxycarbonyl, 2-phenylprop-2-xyloxycarbonyl, 2-(p-toluyl)prop-2- yloxycarbonyl, cyclopentyloxycarbonyl, 1-methylcyclopentyloxycarb cyclohexyloxycarbonyl, 1-methylcyclohexyloxycarbonyl, 2-methylcyclohexyloxycarbonyl, 2-(4-toluylsulfonyl)ethoxycarbonyl, 2-(methylsulfonyl)ethoxycarbonyl, 2-(triphenylphosphino) ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-l-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; the benzoylmethylsulfonyl group, the 2-(nitro)phenylsulfenyl group, the diphenylphosphine oxide group, and like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the t-butoxycarbonyl, and phenoxyacetyl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

In the above process, the term "amide-protecting group" refers to groups typically used to protect the amide nitrogen of a $\beta$-lactam moiety. Such protecting groups include tri($C_1$-$C_6$ alkyl)silyl groups, such as trimethylsilyl, triethylsily, t-butyldimethylsilyl (TBDMS), trityl, allyl, or benzyl. Also encompassed by the term "amide-protecting group" are groups which serve to protect the $\beta$-lactam nitrogen from unwanted side reactions but which are normally not thought of as mere protecting groups, but rather are groups which possess useful functionality for further synthesis. Such groups include the $C_1$-$C_6$ substituted alkyl group and the the $C_1$-$C_6$ alkyl group.

As used herein, the term "protected carboxy group" refers to one of the ester derivatives of the carboxylic acid group commonly employed to block or protect the carboxylic acid group while reactions are carried out on other functional groups on the compound. Examples of such carboxylic acid-protecting groups include allyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxyobenzhydryl, 2,2'4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl) methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject the carboxy-protected molecule to strong nucleophilic bases. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The term "protected hydroxy group" refers to a hydroxy group protected with a conventional protecting group. (See, for example, *Protective Groups in Organic Synthesis* by Theodora W. Greene, New York, John Wiley & Sons, 1981, Ch. 2.)

The term "strong base" includes such reagents as n-butyl lithium, t-butyllithium, sec-butyllithium, lithium diisopropyl amine, lithium hexamethyldisilazane, and the like. The only functional limitation on said reagent is that it not react in a destructive manner with other functionality in the molecule.

In the above process, the term "leaving group" (L) has conventional meaning; i.e., L can be chloro, bromo, iodo, mesyl, tosyl, imidazolo, trifluoromethanesulfonyl, and the like.

The term "hydride reducing agent", as used herein, refers to compounds such as $NaBH_4$, $NaCNBH_3$,

Zn(BH$_4$)$_2$, LiAlH[O-C(CH$_3$)$_3$]$_3$, n-Bu$_4$NBH$_4$, KB[CH(CH$_3$)C$_2$H$_5$]$_3$ H(K-Selectride®), LiCNBH$_3$, LiAlH$_4$ [(CH$_3$OCH$_2$CH$_2$O)$_2$AlH$_2$]Na, LiB(CH$_3$CH$_2$)$_3$H, (CH$_3$)$_4$NBH$_4$, diborane, Na(CH$_3$O)$_3$BH, lithium trisiamylborohydride, diisobutylaluminium hydride, potassium trisiamylborohydride, Ca(BH$_4$)$_2$, NaBH$_4$—CeCl$_3$, and the like.

The choice of hydride reducing agent in the above process step (b) is crucial in determining stereo-selectivity of the eventual orientation of the group represented by R$^2$. For example, utilization of LiAlH-[OC(CH$_3$)$_3$]$_3$ provides predominantly cis ($\beta$, $\beta$) isomer while tetra-n-butyl ammonium borohydride provides predominantly ($\beta$, $\alpha$) (3 and 4 positions, respectively) trans-isomer. Further, reduction of substrates of formula II above wherein R$^2$ and R are trans ($\beta$, $\alpha$or) under appropriate conditions, for example lithium aluminum tri-t-butoxy hydride, results in essentially all cis ($\beta$, $\beta$) product. Thus, as a preferred aspect of the present invention, the second step (B) of the above process proceeds in an essentially stereoselective manner to provide compounds of the formula

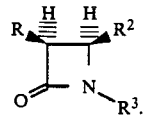

Further, in another preferred aspect of the present invention, the second step (B) of the above process proceeds to provide compounds where R$^2$ is $\alpha$, by using, for example, tetra-n-butylammonium borohydride.

Thus, tetra-n-butylammonium borohydride and LiAlH[OC(CH$_3$)$_{3\beta}$, $_\alpha$]$_3$ are most highly preferred as hydride reducing agents.

As a further aspect of the present invention, there are provided intermediates of Formula (III)

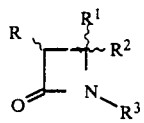

wherein R, R$_1$, R$^2$, and R$_3$ are as defined above, which are formed as a result of step (A) of the process as described above.

In the process of the present invention, the starting materials of formula (II) may be obtained using chemical methodology known in the $\beta$-lactam art. See, for example, preparation 2, below. In like manner, compounds of formula II where R$^1$ is other than phenylsulfonyl may be synthesized using known methodology.

The first step in the process involves alkylation of a compound of formula (II). This reaction is preferably run at reduced temperature in polar aprotic solvents such as tetrahydrofuran, diethyl ether, dimethoxyethane, and the like. A strong base such as n-butyllithium is preferred, although other bases as described herein will also be efficacious. If the orientation of the R group is $\beta$ and the R$^1$ group is $\alpha$, the alkylation will result in a product wherein R$^1$ is essentially in the $\beta$ orientation, although small amounts of $\beta$, $\alpha$(R, R$^1$) can be isolated.

Irrespective of the orientation of the alkylation product (formula III), reduction will provide either cis ($\beta\beta$) or trans ($\beta$, $\alpha$) material, which can then be used as an intermediate for the synthesis of a wide variety of desirable $\beta$-lactam antibiotics such as the monobactams, carbapenems, and 1-carba(1-dethia)-cephalosporins. One reduction method utilizes a hydride reducing agent as described above. Accordingly, as a preferred aspect of the present invention, there is provided the utilization of LiAlH(—O—C(CH$_3$)$_3$1)$_3$ to afford compounds of formula 1 wherein R and R$^2$ are both cis, $\beta$,$\beta$. In this regard, the various R$^2$ groups can then be derivatized into other useful $\beta$-lactam intermediates.

For example, if R$^2$ is 4-butene-1-yl, (A)

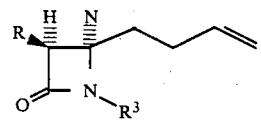

oxidation with KMnO$_4$ will provide cis-4-oxo-3-[(protected) amino]-2-azetidine propanoic acid (B)

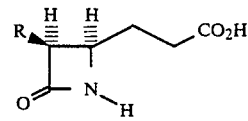

which can be used in the synthesis of penems and 1-carba(1-dethia) cephalosporins. (See for example, C. C. Bodurow, et al., Tetrahedron Letters, Vol. 30, No. 18, pp. 2321–2324, 1989).

Another method of reduction (removal) of the R$^1$ group is the conventional dissolving metal reduction, for example Na amalgam/ethanol. See, for example, J. Chem. Soc., 4881, 1952; Tetrahedron Letters, p. 835, 1973; or Journal of Organic Chemistry, 38, 2447 1(1973l).

Finally, the R$^1$ group in formula (2) may be removed by electrolytic means. For example the method of Justice, et al., as taught in U.S. Pat. No. 4,588,484, incorporated herein by reference, may be utilized to reduce (remove) the R$^1$ group after alkylation (insertion of R$^2$).

The following Examples are set forth to further illustrate the invention but are in no manner to be construed as limiting the scope thereof. The following abbreviations are used herein: NMR=nuclear magnetic resonance spectrum; IR=infrared spectrum; UV=ultraviolet spectrum; MS=mass spectrum; OR=optical rotation.

EXPERIMENTAL SECTION

Preparation 1

41-(S)-Acetoxyazetidinones

The title compounds may be synthesized from penicillin via the methodology taught in Blaszczak, U.S. Pat. No. 4,771,135, especially columns 15–18, incorporated herein by reference.

Preparation 2

3-$\beta$-Phenoxyacetylamino-4-$\alpha$-phenylsulfonylazetidin-2-one

A 27.0 g (100 mM) sample of 3-$\beta$-phenoxyacetylamino-4-$\alpha$-acetoxy-azetidin-2-one was dissolved in 250 ml of dimethylformamide along with 16.4 g (100 mM) of sodium phenylsulfinate and stirred at room temperature for 24 h. The reaction mixture was then diluted with H₂O and extracted with ethyl acetate (3X 500 mL). The combined ethyl acetate portions were then washed sequentially with 1N HCl (1X), H₂O (5X) and brine (1X), dried over anhydrous MgSO₄, filtered and partially concentrated. The mother liquors were then diluted with hexane and the resulting solid filtered and dried in vacuo. Yield =29.1 g (81%) of a yellow powder.

¹H NMR: (300 MHZ, (CH₃)₂SO-d₆) δ9.38 (S, 1H), 8.98 (d, J=7 Hz, 1H), 7.95-6.90 (M, 10H), 5.02 (d, J=1Hz,1H), 4.99 (dd, J=7, 1Hz, 1H) and 4.57 (ABq, 2H).

IR: (KBr) 3299, 3294, 1807, 1781, 1696, 1532, 1491, 1445, 1312, 1303, 1249, 1230, 1149, 1085, and 1066 cm⁻¹.

UV: (ethanol) λ max 322(ε=209), 267 (ε=2160), and 217 (ε=17100)

MS: m/e 360 (M+)

OR: [α]$_D$= −29.9°(C=0.5 in DMSO)

Anal: (C₁₇H₁₆N₂O₅S) C,H,N.

Preparation 3

1-t-Butyldimethylsilyl-3-α-phenoxyacetylamino-4-β-phenylsulfonylazetidin-2-one

A 28.5 g (79.16 mM) sample of 3-β-phenoxyacetylamino-3-α-phenylsulfonylazetidin-2-one and 25 ml of diisopropylethylamine were dissolved in 250 ml of tetrahydrofuran and treated with 13.13 g (87.08 mM) of t-butyldimethylsilyl chloride and allowed to stir at room temperature for 24 h. The solvent was removed in vacuo and the residue was triturated with hexane, dissolved in ethyl acetate, washed sequentially with 1NHCl, H₂O, and brine. The ethyl acetate solution was then dried over anhydrous Na₂SO₄, filtered and concentrated to afford a yellow foam.

The resulting foam was triturated with hexane and purified by liquid chromatography over normal phase silica gel (CH₂Cl₂/ethyl acetate) to afford 29.0 g (77%) of the title compound as a yellow-white solid.

¹H NMR: (300 MHz, CDCl₃) δ 8.0-6.7 (M, 11H), 5.02 (d, J=1Hz, 1H), 4.78 (dd, J=7, 1Hz, 1H), 4.38 (ABq, 2H), 1.06 (S, 9H), 0.4 (S,3H), and 0.3 (S,3H).

IR: (CHCl₃) 1776, 1695, 1599, 1524, 1495, 1471, 1448, 1441, 1323, 1310, 1287, 1256, 1235, 1228, 1217, 1214, 1211, 1209, 1175, 1156, 1082, 1062, 896, 827, 814 and 807

UV: (ethanol) λmax 266 (ε=2060) and 217 (ε=18,100).

MS:m/e 417 (m—C₄H₉)

OR: [α]$_D$= +5.5° (C=0.5 in methanol)

Anal: (C₂₃H₃₀N₂O₅SSi) C, H, N

EXAMPLE 1

3-β-Phenoxyacetylamino-4-β-1-butene-4-yl-azetidin-2-one

A. Alkylation

A 0.995 g (2.096 mM) sample of 1-t-butyldimethylsilyl-3-β-phenoxyacetylamino-4-α-phenylsulfonyl azetidin-2-one was dissolved in 10 ml of tetrahydrofuran and cooled to −78° C. A 3.36 ml (1.56 M in hexane, 5.24 mM) sample of n-butyllithium was then added and the solution stirred for 30 min. and then treated with 0.425 ml (4.192 mM) of 4-bromo-1-butene. The reaction mixture was allowed to stir at −78° C. for 5 min., and then at −28° C. for 5 h. The reaction mixture was then quenched with pH 4 buffer, extracted with ethyl acetate (3X). The combined ethyl acetate portions were dried over anhydrous MgSO₄, filtered, and concentrated in vacuo. Trituration of the resulting solid with diethyl ether provided 393.4 mg. The mother liquors were crystallized in diethyl ether to provide 119.5 mg (combined yield =47%) of 1-t-butyldimethylsilyl-3-β phenoxyacetylamino-4-phenylsulfonyl-4-β-(1-butene-4yl)-azetidin-2-one.

¹H NMR: (300 MHZ, CDCl₃) δ 8.05 (d, J=8 Hz, 1H), 7.8-6.6 (m,10H), 6.15 (d, J=8 Hz, 1H), 5.42 (m, 1H), 4.98 (dd, J=6, 1 Hz, 1H), 4.92 (dd, J=12, 1 Hz 1H), 4.4 (ABq, 2H), 2.3 (m, 1H), 2.15 (M, 1H), 1.85 (M, 1H), 3.35 (M, 1H), 1.1 (S,9H), 1.45 (S,3H), 1.40 (S,3H).

IR: (CHCl₃): 2960, 2932, 1766, 1701, 1599, 1517, 1494, 1472, 1447, 1441, 1321, 1311, 1291, 1264, 1257, 12 1216, 1206, 1204, 1174, 1152, 1083, 845, 834, 823, and 810 cm⁻¹.

UV: (ethanol) λ max 274 (ε=1890), 267 (ε=2260), and 218 (ε=18,000).

MS: m/e 471 (M—C₄H₉)

OR: [α]$_D$= +16.0° (C=0.5 in methanol)

Anal: (C₂₇H₃₆N₂O₅SSi) C, H, N

B. Deprotection

A 2.00 g (3.795 mM) portion of the product of Part B above, was dissolved in 100 ml of (1:1) tetrahydrofuran/1N HCl and stirred at 0° C. for 30 min., then at room temperature for 5 h. The solvent was removed in vacuo (azeotroped with toluene and benzene) to afford 1.69 g of 3-β-phenoxyacetylamino-4-αphenylsulfonyl-4-β-(1-butene-4-yl-azetidin-2-one.

¹H NMR: (300 MHz, (CH₃)₂ SO—d₆) δ 9.75 (S, 1H), 9.18 (d, J=8 Hz, 1H), 8.0-6.8 (M, 10H), 5.7 (m, 1H), 5.4(d, J=8 Hz, 1H), 4.9 (M, 2H), 4.6 (ABq, 2H), 2.2 (M, 2H), 1.9 (M, 1H), and 1.65 (M, 1H).

IR: (CHCl₃): 1792, 1700, 1516, 1495, 1234, 1230, 1226, 1205, and 1153 cm⁻¹.

UV: (ethanol) 80 max 275 (ε=2440), 268 (ε=2760), and 216 (ε=16,800)

MS: m/e 415 (M+)

OR: [α]$_D$= −1.4 (C=0.5 in methanol)

Anal: Calc. or C₂₁H₂₂N₂O₅S: C, 60,86; H, 5.35; N, 6.76. Found C,59.47; H,5.66; N, 7.60.

C. Reduction

A 1.00 g (2.245 mM) sample of the crude product from Part B above, was dissolved in 15 ml of tetrahydrofuran and cooled to 0° C. To this solution was added 1.23 g of lithium tri-tert-butoxyaluminohydride. The reaction mixture was stirred at 0° C. for about 30 min., and then quenched with saturated aqueous NaHCO₃ solution and diluted with ethyl acetate and 1NNaOH. The aqueous layer was extracted (3X) with CH₂Cl₂/isopropanol and the combined organic layers were, in turn, washed with brine, dried over anhydrous MgSO₄, filtered and concentrated in vacuo. The resulting residue was triturated with hexane (1X) and then with diethyl ether (3X), thereby removing trans-substituted contaminant. The resulting solid was dried in vacuo to provide 480.0 mg (78% yield) of 3-β-phenoxyacetyl-4-β-(1-butene-4-yl)azetidin-2-one.

¹H NMR (300 MHZ, (CH₃)₂ SO—d₆) δ 8.9 (d, J=8 Hz, 1H), 8.4 (S, 1H), 7.3 (M, 2H), 6.95 (M, 3H), 6.75 (M, 1H), 5.10 (dd, J=8, 4 Hz, 1H), 5.02-4.90 (M, 2H), 4.56 (S, 2H), 3.64 (M, 1H), 2.0 (M, 2H), and 1.5 (M, 2H).

IR: (CHCl$_3$): 1770, 1689, 1495, 1236, 1224, 1220, 1217, 1213, and 1210 cm$^{-1}$.
UV: (ethanol) λ max 275 (ε=1200) and 269 (ε=1430).
MS:m/e 274 (M+)
OR: [α]$_D$=61.9° (C=0.5 in methanol)
Anal: (C$_{15}$H$_{18}$N$_2$O$_3$) C, H, N.

Preparation 4

3-β-Phenoxyacetylamino-4-β-[2-carboxyethyl]azetidin-2-one

A 31.9 mg (0.116 mM) of the product of Example 1 was combined with 8 ml of (1:1) acetone/H$_2$O, 0.2 ml of acetic acid, and 73.5 mg (0.466 mM) of KMnO$_4$ and stirred at 0° C. for 6 h. The reaction mixture was then quenched with sodium sulfite/1NHCl/ethyl acetate. The ethyl acetate layer was dried over anhydrous MgSO$_4$, filtered, and concentrated in vacuo to afford a white solid. The resulting solid was triturated with ethyl ether and dried in vacuo to afford 23.4 mg (70% yield) of the title compound.

$^1$H NMR: (300 MHz, (CH$_3$)$_2$ SO-d$^6$) 12.15 (brS, 1H), 8.92 (d, J=8H, 1H), 8.38 (S, 1H), 7.3 (M,2H), 6.92 (M, 3H), 5.08 (dd, J=8, 4Hz 1H), 4.57 (ABq, 2H), 3.64 (m, 1H), 2.2 (M, 2H), and 1.65 (M, 2H) IR: (KBr): 3321, 3091, 3085, 3077, 1744, 1736, 1715, 1665, 1533, 1489, 1405, 1235, 1194, 1181, and 1174 cm$^{-1}$.
UV: (methanol) λ max 275 (ε=1040), 268 (ε=1280, and 217 (ε=758)
MS: m/e 274 (M +—OH) Anal: (C$_{14}$H$_{16}$N$_2$O$_5$) C, H, N.

EXAMPLE 2

3-β-Phenoxyacetylamino-4-α-phenylsulfonyl-4-β-(3-phenyl-2-propene-1-yl)-1-t-butyldimethylsilyl-azetidin-2-one A. Alkylation A 1.00g (2.11 mm) sample of 1-t-butyldimethylsilyl-3-β-phenoxyacetylamino-4-α-phenylsulfonyl-azetidin-2-one was dissolved in 10 ml of THF, cooled to −78° C., and treated with 4.7 ml (6.33 mm; 1.11M in hexane) of n-butyllithium and stirred for about 10 min. The reaction mixture was then treated with 415.8 mg (2.11 mm) of cinnamyl bromide and stirring was continued at −28° C. for 2h, followed by the addition of 200 mg of cinnamyl bromide. The reaction mixture was then quenched with pH4 buffer and extracted with Ch$_2$Cl$_2$. The CH$_2$Cl$_2$ portion was washed with brine, dried over anhydrous MgSO$_4$, filtered, and concentrated in vacuo to afford 1.3075g of 1-t-butyldimethylsilyl 3-β-phenoxyacetylamino-4-α-phenylsulfonyl-4-α-(3-phenyl-2propene-2-one as a yellow oil, used in the next step without purification.

B. Deprotection

The product from part A above was dissolved in a mixture composed of 10 ml of 1N HCl and 10 ml of THF and stirred at room temperature for 20h. The reaction mixture was then diluted with ethyl acetate and brine, salted, and extracted (3×) with ethyl acetate. The combined ethyl acetate portion was dried over anhydrous MgSO$_4$, filtered, and concentrated in vacuo to afford 1.26 of 3-β-phenoxyacetylamino-4-α-phenyl-sulfonyl-4-α-(3-phenyl-2-propene-1-yl)-azetidin-2-one as a yellow solid, used in the next step without purification.

C. Reduction

A 1.26g sample of the material from part B, above, was dissolved in 30 ml of THF and cooled to 0° C. The substrate was then treated with 1.61 g (6.33 mm) of lithium tri-tert-butoxy aluminum hydride in portions and stirred at 0° C. for 4h, then at room temperature for 16h. The reaction mixture was then quenched with acetone, then ethyl acetate, then aqueous NaOH. The reaction mixture was then extracted with ethyl acetate (4×) and the combined ethyl acetate portions were washed with brine, dried over anhydrous MgSO$_4$, filtered, and concentrated in vacuo to afford 890 mg of a yellow solid.

This crude product was boiled in 25 ml of diethyl ether and then cooled. The resulting precipitate was triturated with diethyl ether to afford 330 mg of a yellow white solid.

$^1$NMR (300 MHz, DMSO-d$_6$): δ 9.0 (d, 1H, J =8 Hz), 8.45 (s, 1H), 7.4–6.8 (m, 10 H), 6.6–6.2 (m, 2H), 5.2 (dd, 1H, J=5, 8 Hz), 4.8 (S, 2H), 3.8 (m, 1H) and 2.35 (m, 2H)
IR (CHCl$_3$): 3420, 3020, 1771, 1686, 1523, 1495, 1237, and 1214 cm$^{-1}$.
MS: m/e 336 (m+)
UV (ethanol) εmax=304(ε=8940), 276 (ε=6650), and 254 (ε=13,700)
OR: [α]$_D$= +16.9 (C=0.59 in CH$_3$OH) Elemen. Anal. (C$_{19}$H$_{20}$N$_2$O$_3$)

| Theory (%) | | Found (%) | |
|---|---|---|---|
| C | 71.41 | C | 69.15 |
| H | 5.99 | H | 5.31 |
| N | 8.33 | N | 7.84 |

EXAMPLE 3

3-Phenoxyacetylamino-4-α-dodecyl-azetidin-2-one

A. Alkylation

A 1.00g (2.11 mm) sample of 3-β-phenoxyacetylamino-4-α-phenylsulfonyl-1-t-butyldimethylsilyl azetidin-2-one was dissolved in 10 ml of THF and treated with n-butyllithium (3.38 ml; 5.275 mm; 1.56 M in hexane) and dodecylbromide (1.01 ml; 1.052 g; 4.22 mm) in the general procedure of Examples 1,2 and 3, to provide, after column chromatography over silica gel (hexane/ethyl acetate) 886.8 mg of 3-β-phenoxyacetylamino- 4-α-phenyl sulfonyl-4-β-dodecyl-1-t-butyldimethylsilyl-azetidin-2-one as a yellow foam. (65% yield)

$^1$H NMR (300 MHz, DMSO-d$_6$) δ 8.05 (d, 1H, J=8 Hz), 7.8–6.6 (m, 10 H), 6.16 (d, 1H, J=8 Hz), 4.4 (ABq, 2H), 1.4–1.0 (m 22 H), 1.1 (S, 9H), 0.9 (t, 3H, J=7 Hz), 0.43 (S, 3H), and 0.39 (S, 3H).
IR (CHCl$_3$): 3024, 2955, 2930, 1766, 1702, 1600, 1518, and 1495 cm$^{-1}$
MS: m/e=643 (M+)
OR: [α]$_D$= +19.9 (C=0.5 in methanol)
UV (ethanol) εmax=315 (ε=2100), 286 (ε=1860), 2550, (ε=2550, and 268 (ε=2430)

B. Deprotection

A 780 mg (1.21 mm) sample of the product from part A, above, was suspended in a mixture of 20 ml THF and 20 ml of 1N HCl and stirred at room temperature for 72h. The reaction mixture was then diluted with ethyl acetate, salted, and extracted (3x) with ethyl acetate. The combined ethyl acetate portions were washed with brine, dried over anhydrous MgSO$_4$, filtered, and concentrated in vacuo to afford 700 mg of 3-β-phenoxyacetyl-4-α-phenylsulfonyl-4-α-dodecylazetidin-2-one as a yellow-white solid.

$^1$H NMR (300 MHz, DMSO-d$_6$) δ 9.65 (S, 1H), 9.1 (d, $^1$H, J=8 Hz), 7.9–6.8 (m, 10H), 5.38 (d, 1H, J=8 Hz), 4.6 (ABq, 2H), 1.6–1.0 (m, 22H), and 0.85 (t, 3H, J=7 Hz)

IR (CHCl$_3$): 3020, 2956, 2929, 2857, 1790, 1702, 1518, and 1495 cm$^{-1}$.

MS: m/e 529 (M+)

OR: [α]$_D$= + +2.8 (C=0.5 in methanol)

UV (ethanol) εmax=268(ε=2050)

C. Reduction

A 206 mg sample of the product from part B, above was dissolved in 10 ml of THF, cooled to 0° C., and treated with 200.2 mg (0.787 mm) of lithium aluminum tri-t-butoxy hydride and stirred for 4h. The reaction mixture was then quenched with NaHCO$_3$ and extracted with ethyl acetate (4×). The combined ethyl acetate portions were dried over anhydrous MgSO$_4$, filtered, and concentrated in vacuo to afford 156.2 mg of the title compound as a white solid.

Preparative thin layer chromatography (ethyl acetate as eluent) afforded 102.9 mg of a white solid (74% yield)

$^1$H NMR (300 MHz, DMSO-d$_6$) δ 8.85 (d, 1H, J=8 Hz), 8.35 (s, 1H), 7.3–6.9 (m, 5 H), 5.05 (dd, 1H, J=8, 5 Hz), 4.55 (S, 2H), 3.6 (m, 1H), 1.4-1.0 (m, 22H), and 0.85 (t, 3H, J=7 Hz)

IR (CHCl$_3$): 3420, 2970, 2856, 1770, 1689, 1525, 1496, and 1238 cm$^{-1}$

UV (ethanol) εmax=268 (ε=1490)

OR: [α]$_D$= +42.9 (C=0.5 in methanol)

MS: m/e 389 (m+)

EXAMPLE 4

3-β-Phenoxyacetylamino-4-α-methoxyethyl-azetidin-2-one

A. Alkylation

A 1.00 g (2.11 mm) sample of 3-β-phenoxyacetylamino -4-α-phenylsulfonyl--t-butyldimethylsilylazetidin-2-one was alkylated with methoxyethylbromide in THF using n-butyllithium as base in a procedure analogous to that used in previous examples. Column chromatography (silica gel, elution with CH$_2$Cl$_2$/ethyl acetate) afforded 641.4 mg of 3-α-phenoxyacetylamino-4-β-phenylsulfonyl-4-β-methoxyethyl-4-t-butyldimethylsilyl-azetidin-2-one as a white solid (57% yield).

$^1$H NMR (300 MHz, DMSO-d$_6$) δ 8.45 (d; 1H, J=8 Hz), 7.9–6.5 (m, 10H), 6.3 (d, 1H, J=8 Hz), 4.38 (ABq, 2H), 3.4 (m, 2H), 3.2 (S, 3H), 2.2–1.4 (m, 2H), 1.1 (S, 9H), 0.42 (S, 3H), and 0.38 (S, 3H)

IR (CHCl$_3$): 2931, 1772, 1690, 1601, 1527, 1494, and 1472 cm$^{-1}$

UV (ethanol) εmax=268 (ε=2040)

OR: [α]$_D$= +55 (C =0.5 in methanol)

MS: m/e 475 (M+—C$_4$H$_9$)

B. Deprotection

A 541.1 mg (1.017 mm) sample of the product from part A, above, was deprotected in a procedure analogous to that of the foregoing examples to provide 431.4 mg of 4-β-phenoxyacetylamino-4-α-phenylsulfonyl 4-β-methoxyethyl-azetidin-2-one as a white solid (101.4%).

$^1$H NMR (300 MHz, DMSO-d$_6$) δ 9.6 (S, 1H), 8.75 (d, 1H, J=8 Hz), 8.0–6.8 (m, 10H), 5.5 (d, 1H, J=8 Hz), 4.6 (ABq, 2H), 3.4 (m, 2H), 3.2 (S, 3H), and 1.9 (m, 2H)

IR (CHCl$_3$): 1794, 1692, 1524, 1495, and 1309 cm$^{-1}$

UV (ethanol) εmax=290 (ε=15,900)

OR: [α]$_D$=14.4 (C=0.5 in methanol)

MS: m/e 276 (M+SO$_2$C$_6$H$_5$)

C. Reduction

A 114.8 mg sample of the product from part B, above, was reduced in a procedure analogous to that of Example 4 above, using lithium aluminum tri-t-butoxy hydride as the reducing agent. Preparative thin layer chromatography (silica gel, ethyl acetate as eluent) afforded 50.9 mg (68% yield) of the title compound as a white solid.

$^1$H NMR (300 MHz, DMSO-d$_6$) δ 8.55 (d, 1H, J =8 Hz), 6.08 (S, 1H), 5.42 (dd, 1H, J =5, 8 Hz), 4.56 (S, 2H), 4.02 (m, 1H), 3.5 (m, 2H), 3.3 (S, 3H), and 1.7 (m, 2H)

IR (CHCl$_3$): 3013, 1770, 1685, 1600, 1496, and 1237 cm$^{-1}$

UV (ethanol) εmax=269 (ε=1290)

OR: [α]$_D$= $^{+41}$ (C=1.0 in methanol)

MS: m/e 278 (M+)

EXAMPLE 5

3-β-Phenoxyacetylamino-4-β-ethyl-azetidin-2-one

A. Alkylation

In a manner analogous to previous examples, a 2.00 g (4.22 mm) sample of 3-β-phenoxyacetylamino-4-α-phenylsulfonyl-1-t-butyldimethylsilyl-azetidin-2-one was alkylated with ethyl bromide in THF using n-butyllithium as base to provide 1.4353g of 3-β-phenoxyacetylamino-4-α-phenylsulfonyl-4-ethyl-1-t-butyldimethylsilyl-azetidin-2-one as a white foam (68%)

$^1$H NMR (300 MHz, DMSO-d$_6$) δ 8.05 (d, 1H, J=8 Hz), 7.8–6.6 (m, 10H), 6.15 (d, 1H, J=8 Hz), 4.4 (ABq, 2H), 2.2 (m, 1H), 1.2 (m, 1H), 1.1 (S, 9H), 0.8 (t, 3H, J=8 Hz), 0.42 (S, 3H), and 0.38 (S, 3H).

IR (CHCl$_3$): 2934, 1765, 1702, 1600, 1519, and 1495 cm$^{-1}$

UV (ethanol) εmax=312 (ε=1010), 268 (ε=2140)

OR: [α]$_D$= +15.9 (C=0.5 in methanol)

MS: m/e 445 (M+C$_4$H$_9$)

B. Deprotection

In a manner analogous to previous examples, a 1.23 g (2.4 mm) sample of the product from part A, above, was deprotected to afford 1.0410 g (112%) of 3-β-phenoxyacetylamino-4-phenylsulfonyl-4-α-ethyl-azetidin-2-one as a white solid, used in the next step without purification.

C. Reduction

In a procedure analogous to Example 5, above, a 134 mg sample of the product from part B, above, was reduced to afford (after preparative thin layer chromatography) 34.8 mg (46% yield) of the title compound.

$^1$H NMR (300 MHz, CDCl$_3$) δ 7.4–7.0 (m, 5H), 6.9 (d, 1H, J=8 Hz), 6.4 (S, 1H), 5.35 (dd, 1H, J =8, 5 Hz), 4.56 (S, 3H), 3.8 (m, 1H), 1.8–1.4 (m, 2H), and 0.9 (t, 3H, J=7 Hz)

EXAMPLE 6

3-β-Phenoxyacetyl-4-(α,β)(1-butene-4-yl)-azetidin-2-one 1-t-Butyldimethylsilyl-3-β-phenoxyacetylamino-4-αphenylsulfonyl-4-β-butenyl-azetidinone was prepared in a manner analogous to Example 1 above.

C. Reduction (1) NaBH₄

A 52.7 mg 0.1 mm sample of 1-t-butyldimethylosilyl-3-β-phenoxyacetylamino-4-α-phenylsulfonyl-4-β-butenyl-azetidin-2-one (prepared in Example 1 above) was suspended in 2 ml of isopropanol and 1 ml of H₂O and treated with a molar excess of NaBH₄. Working up as before showed a mixture of cis (40.5%) and trans (59.5%) products (i.e., α and β butenyl substituted azetidinone).

(2) NaCNBH₃

A 50.0 mg sample of 1-t-butyldimethylsilyl3β-phenoxyacetylamino-4-α-phenylsulfonyl-4-β-butenylaztidin -2-one was dissolved in 2 ml of isopropanol and 1 ml of H₂O and treated with NaCNBH₃. Workup and analysis indicated a cis/trans mixture with cis predominating (60/40 cis/trans).

(3) Zn(BH₄)₂

In a procedure analogous to 7(C)(1) and (2) above, the utilization of Zn(BH4)₂ as reducing agent afforded a product comprised of mainly cis isomer (70/30 cis/trans).

(4) N(CH₃CH₂CH₂CH₂)₄BH₄

In a procedure analogous to 7(C) 1, 2, and 3, above N(CH₃CH₂CH₂CH₂)₄BH₄ was utilized as the reducing agent. This reaction afforded predominantly trans material, i.e., 3-β-phenoxyacetylamino-4-α-butenylazetidin-2-one (87/13 trans/cis).

EXAMPLE 7

3-β-Phenoxyacetylamino-4-β-benzyl-azetidin-2-one

A. Alkylation

In a procedure analogous to the foregoing examples, 1 g (2.11 mm) of 3-β-phenoxyacetylamino-4-α -phenyl-sulfonyl-1-t-butyldimethylsilyl-azetidin-2-one was alkylated with benzyl bromide to afford 1.14 g of a yellow oily solid. Trituration of the crude product with diethyl ether provided the pure product.

m.p.=121°-122° C.
NMR: 300 MHz (CDCl₃): δ 0.54 (S, 3H); 0.55 (S, 3H); 1.16 (S,9H); 2.83 and 3.80 (ABq, 2H, J=15 Hz); 4.19 and 4.29 (ABq, 2H, J=18Hz); 6.29 (d, 1H, J=9Hz); 6.38 (d, 1H, J=9 Hz); 6.53 (d, 2H, J=6 Hz); 6.94-7.25 (m, 8H); 7.60-7.79 (m, 3H); 8.14 (d, 2H, J=6 Hz)
IR: (CHCl₃): 3017, 1770, 1696, 1517, 1496, 1310, 1150 cm⁻¹
MS: (FD) m/e=422 (m-142 (—SO₂ phenyl))
UV: (ethanol) λ=268nm (ε=2440) λ=274nm (ε=2030)
OR: (methanol)= +82.68° at 365 nm
Elem. Anal. calc'd: C:63.80 H:6.43 N:4.96 obs'd: C:64.08 6.54 N:4.87

B. Deprotection and C. Reduction

The product from Part A above, is deprotected and reduced in a manner analogous to that taught in Example 4 to afford the title compound.

EXAMPLE 8

3-β-Phenoxyacetylamino-4-β-allyl-azetidin-2-one

A. Alkylation

In a procedure analogous to Example 4, above, a 5.0 g (10.55 mm) sample of 3-β-phenoxyacetylamino-4-α-phenylsulfonyl-1-t-butyldimethylsilyl-azetidin-2-one was allylated with allyl bromide to form 3-β-phenoxyacetylamino-4-α-phenylsulfonyl-4-α-allyl-1-t-butyl-dimethylsilyl-azetidin-2-one as a dark yellow oil.

m.p.=94°-96.5° C.
NMR: 300 MHz (CDCl₃): δ 0.44 (S, 3H); 0.48 (S, 3H); 1.11 (S, 9H); 2.06-2.14 (M, 1H); 3.10-3.22 (M, 1H); 4.27 and 4.45 (ABq, 2H, J=15 Hz); 4.86-4.95 (M, 1H); 5.24-5.31 (M, 1H); 5.64-5.88 (M, 1H); 6.26 (d, 1H; J=12 Hz); 6.64(d, 2H, J=9 Hz); 6.94-7.26 (M, 3H); 7.10 (d, 1H, J=12 Hz); 7.58-7.78 (M, 3H); 8.60 (d, 2H, J=6 Hz)
IR: (CHCl₃):2970, 2940, 1770, 1698, 1519, 1495, 1310, 1155 cm³¹ ¹
MS (FD): m/e=515 (m+1)
UV (ethanol): λ=217 nm (ε=15,100); λ=267 nm (ε=1930); λ=274 nm (ε=1650);
OR (methanol): +90.04° at 365 nm
Elem. Anal. calc'd: C:60.67 H:6.66 N:5.44 obs'd: C:60.96 H:6.84 N:5.45

B. Deprotection (1) A 4.76 g (11.9 mm) sample of the product from Part A, above, was dissolved in a mixture comprised of 125 ml of THF and 125 ml 1N HCl and stirred at room temperature for 7¼ h. The reaction mixture was then diluted with water and extracted with CH₂Cl₂. The combined organic phase was washed with brine, dried over anhydrous MgSO₄, filtered, and concentrated in vacuo to provide a yellow semi-solid. Trituration of the product with diethyl ether afforded 1.66 g of a cream-colored solid.

(2) A deprotection and reduction of the product of Procedure A, above, utilizing Red-Al ® (sodium bis(2-methoxyethoxy) aluminum hydride) provided 3-β-phenoxyacetylamino-4-α-β-allyl-azetidin-2-one.

(3) A deprotection and reduction of the product of Procedure A, above, using lithium aluminium tri-t-butoxy hydride provided 3-β-phenoxyacetylamino-4-β-allyl-azetidin-2-one as the predominant product (ration of cis: trans =89:11).

m.p.=142°-144° C.
NMR 300 MHz (CDCl₃): δ 2.04-2.18 (M, 1H); 2.28-2.39 (M, 1H); 3.92-4.00 (M, 1H); 4.54 (S, 2H); 5.04-5.17 (M, 2H); 5.33-5.41 (M, 1H); 5.64-5.79 (M, 1H); 6.10 (br s, 1H); 6.89-7.38(M, 6H)
IR (CHCl₃): 3023, 1773, 1688, 1600, 1524, 1496, 1237 cm⁻¹.
MS (FD): m/e=260 (M+)
UV (ethanol): λ=269 nm (ε=1430); λ=275 nm (ε=1180)
OR (DMSO): +263.9 at 365 nm
Elem. Anal. calc'd: C:64.60 H:6.20 N:10.76 obs'd: C:64.83 H:6.16 N:11.00

(4) A deprotection and reduction of the product of Procedure A, above, using NaBH₄ provided 3-β-phenoxyacetylamino-4-α-β-allyl-azetidin-2-one in a 1:1.7 ratio (cis:trans).

EXAMPLE 9

3-β-Phenoxyacetylamino-4-α-allyl-azetidin-2-one

A 78 mg (0.195 mm) sample of 3-β-phenoxyacetylamino-4-α-allyl-4-α-phenylsulfonyl-azetidin-2-one was dissolved in 3 ml of THF and cooled to 0° C. The substrate was then treated with 110 mg (0.428 mm) of lithium aluminum tri-t-butoxy hydride and stirred for about 45 min. The reaction mixture was then quenched with saturated NaHCO$_3$ solution and poured into an ethyl acetate/water mixture. The resulting mixture was made basic with 2N NaOH, and the organic layer separated. The aqueous phase was extracted twice more with ethyl acetate and the combined organics washed with brine, dried over anhydrous Na$_2$SO$_4$, filtered, and concentrated in vacuo. Column chromatography (9:1, ethyl acetate:hexane) provided 31 mg of the title compound.

NMR: 300 MHz (CDCl$_3$) δ =2.07–2.2 (M, 1H); 2.30–2.40 (M, 1H); 3.82–4.01 (M, 1H); 6.31 (S, 1H); 6.90–7.41 (M, 6H)

IR (KBr): 3212.4, 1761, 1750, 1661, 1547, 1498, 1245, 1231 cm$^{-1}$

MS (FD): m/e=260 (M+)

UV ethanol): λ=268 nm (ε=1250) λ=275 nm (ε=1020)

OR (DMSO): +77.84° at 589 nm; +245.51° at 365 nm;

Elem. Anal. calc'd: C:64.60 H:6.20 N:10.76 obs'd: C:64.83 H:6.17 N:10.52

EXAMPLE 10

3-β-Phenoxyacetylamino-4-α-methyl-azetidin-2-one

A. Alkylation

In a procedure analogous to Example 4, above, a 1.0 g (2.11 mm) sample of 3-β-phenoxyacetylamino-4-β-phenylsulfonyl-1-t-butyl dimethylsilyl-azetidin-2-one was alkylated with methyl iodide to form 3-β-phenoxyacetylamino-4-α-phenylsulfonyl-4-α-methyl-1-t-butyl-dimethylsilyl-azetidin-2-one.

m.p.=dec.>76° C.

NMR 300 MHz (CDCl$_3$): δ 0.40 (S, 3H); 0.42 (S, 3H) 1.05 (5.9H); 1.40 (S.3M); 4.34 and 4.43 (Abq. 2H, J=15 Hz); 5.64 (d, 1M, J=9 Hz); 6.69–7.24 (M, 6H); 7.57–8.00 (M, 5H)

IR (KBr) 2930, 2860, 1768, 1749, 1691, 1308, 1254.5, 1153, 1069 cm$^{-1}$

MS (FAB) m/e=489 (M +), 347 (—SO$_2$)

UV (ethanol) λ=218 nm (ε=16400); λ=267 nm (ε=2020), λ=274 nm (ε=1660)

OR (DMSO): +41.98° at 589 nm; +171.76° at 476 nm,

Elem. Anal. Calc'd: C:58.99 H:6.60 N:5.73 Obs'd: C:59.19 H:6.73 N:5.68

B. Deprotection

In a manner analogous to Example 11, below, the product from Part A, above, was deprotected.

NMR 300 MHz (DMSO-d$_6$): δ 1.33 (S, 3H); 4.51 and 4.56 (Abq, 2H, J=9 Hz); 5.35 (d, 1H, J=9 Hz); 6.83–7.23 (M, 5H); 7.62–7.86 (M, 5H); 9.04 (d, 1H, J=9Hz 9.41(S, 1H)

IR (KBr) 3280, 3100, 1764, 1672, 1496, 1447, 1239, 1151, 1071 cm$^{-1}$

MS (FD): m/e=374 (M+), 232 (—SO$_2$-phenyl)

UV (ethanol) λ=216 nm (ε=18300); λ=268 nm (ε=2230); λ=275 cm (ε=1940)

OR (DMSO): +21.87° at 589 nm +117.30° at 375 nm,

Elem. Anal. calc'd: C:57.74 H:4.85 N:7.48 ; obs'd: C:57.46 H:4.59 N:7.31

C. Reduction

In a manner analogous to Example 11, below, the product from Part B, above was reduced to provide the title compound.

m.p.=192–194° C.

NMR 300 MHz (DMSO-d$_6$): δ 6 0.99 (d, 3H, J=6Hz); 3.70–3.74 (M, 1H); 4.52 (S, 2H); 4.96–5.01 (M, 1H); 688–7.27 (M, 5H); 8.17 (S,1H); 8.81 (d, 1H, J=3 Hz)

IR (KBr) 3273, 2970, 1754, 1759, 1547, 1500, 1254 cm$^{-1}$

MS m/e=235 (M +)

UV λ=269 nm (ε=1360) λ=275 nm (ε=1130)

OR (DMSO): +80.00° at 589 nm; +218.18° at 365 nm

Elem. Anal. calc'd: C:61.53 H:6.02 N:11.96 ; obs'd C:61.25 H:5.78 N:11.67

EXAMPLE 11

3-β-Phenoxyacetylamino-4-β-(4-pentene-1-yl)-azetidin-2-one

A. Alkylation

A 1.0 g (2.11 mm) sample of 3-β-phenoxyacetylamino-4-a-phenylsulfonyl-1-t-butyldimethyl-silylazetodom- 2-one was dissolved in 10 ml of THF and cooled to −78° C. The substrate was then treated with 3.5 ml (1.49 M in hexane; 5.27 mm) of n-butyllithium and stirred for about 30 min. The reaction mixture was then treated with 0.28 ml (2.33 mm) of 5-bromopent-1-ene and warmed to −0° C. After about 2.5 h, the reaction mixture was quenched with pH 4 buffer, diluted with water and extracted (3 ×) with CH$_3$Cl$_2$. The combined organics were washed with brine, dried over anhydrous MgSO$_4$, filtered and concentrated in vacuo. Purification of the crude product afforded 773 mg (68%) of 3-β-phenoxyacetylamino-4-β-phenylsulfonyl-4-β-(4-pentene-1-yl)-1-t-butyldimethylsilyl-azetidin-2-one.

m.p. =129°–132° C.

NMR 300 MHz (CDCl$_3$): δ 0.38 (S, 3M); 0.42 (S, 3H); 1.07 (S,9H); 0.87–1.25 (M, 2H); 1.39–1.50 (M, 1H); 1.67–1.79 (M, 2H); 2.10–2.23 (M, 1H); 4.27 and 4.49 (ABq, 2H, J=15 Hz); 4.8–4.92 (M, 2H); 5.50–5.63 (M, 1H); 6.13 (d, 1H, J=12 Hz); 6.59–7.18 (M, 6H); 7.57–8.03 (M, 5H)

IR (KBr): 1758, 1745, 1695, 1495, 1257, 1253, 1151, 2865, 2960 cm$^{-1}$

MS (FAB) m/e=543 (M +), 401 (—SO$_2$phenyl)

UV (ethanol) λ=217 nm (ε=16900); λ=267 nm (ε=2110); λ=274 nm (ε=1850)

OR (DMSO): +11.90° at 589 nm +61.90° at 365 nm

Elem. Anal. calc'd: C:61.96 H:7.06 N:5.16; obs'd: C:62.20 H:6.91 N:5.35

B. Deprotection

A 680 mg (1.25 mm) sample of the product from Part A, above, was dissolved in a mixture of 25 ml of 1N HCl and 15 ml of THF and stirred overnight. The reaction mixture was then diluted with water and extracted twice with CH$_2$Cl$_2$. The combined organics were then washed with brine, dried over anhydrous MgSO$_4$, filtered, and concentrated in vacuo to provide a white solid. Trituration with diethyl ether and subsequent drying afforded 396 mg of 3-β-phenoxyacetylamino-4-α-phenylacetylamino-4-β-(4-pentene-1-yl)-azetidin2-one.

m.p. =146°–148° C.

NMR 300 MHz (CDCl$_3$): δ 1.35–1.97 (M, 4H); 4.49 (S, 2H); 4.89–4.95 (M, 2H); 5.57 (d, 1H, J=9 Hz); 5.56–5.70 (M, 1H); 6.77–7.32 (M, 6H); 7.60–8.12 (M, 5H)

IR (KBr) 3300, 3200, 1776, 1668, 1535, 1496.5, 1306, 1228, 1148 cm$^{-1}$

MS m/e=429 (M +), 287 (—SO$_2$ phenyl)

UV (ethanol) λ=216 nm (ε=17900); λ=268 nm (ε=2190); λ=275 nm (ε=1920)

OR (DMSO) +17.93° at 589 nm +71.71° at 365 nm

Elem. Anal. calc'd: C:61.67 H:5.65 H:6.54; obs'd: C:61.86 H.5.70 N:6.49

C. Reduction

A 355 mg sample of the product from Part B, above, was dissolved in 7 ml of THF and cooled to about 0° C. The substrate was then treated with lithium aluminum tri-t-butoxy hydride and stirred for about 45 min. The reaction mixture was then quenched with saturated NaHCO$_3$ solution, diluted with 2N NaOH and extracted with ethyl acetate (2 ×). The combined organics were then washed with brine, dried over anhydrous MgSO$_4$, filtered, and concentrated in vacuo to provide the crude product. Column chromatography (silica gel, 80% ethyl acetate, 20% hexane) provided 184 mg (77% yield) of the title compound as a white solid. The crude product appears to have been produced in a ratio of cis:trans of 93:7.

m.p. =114°–117° C.

300 MHz (CDCl$_3$): δ 1.32–1.53 (M, 4H); 1.98–2.04 (M, 2H); 3.82–3.87 (M, 1H); 4.53 (S, 2H); 4.92–5.00 (M, 2H); 5.31–5.35 (M, 1H); 5.66–5.79 (M, 1H); 6.16 (S, 1H); 6.90–7.34 (M, 5H); 7.16 (d, 1H, J=9 Hz)

IR (KBr): 3230, 2940, 1763, 1753, 1657, 1545, 1498, 1240 cm$^{-1}$

MS (FD) m/e 288 (M+)

UV λ=269 (ε=1370) λ=275 (ε=1130)

OR +80.55° at 589 nm; +264.24° at 365 nm

Elem. Anal. calc'd: C:66.65 H:6.99 N:9.72; obs'd: C:66.68 H:6.78 N:9.63

EXAMPLE 12

3-β-Phenoxyacetylamino-4-α-methyl-azetidin-2-one

A 600 mg sample of 3-β-phenoxyacetylamino-4-α-phenylsulfonyl-4-α-methyl-azetidin-2-one (see Example 11) (1.60 mm) was dissolved in 40 ml of THF, cooled to 0° C. and treated with 825 mg (3.20 mm) of tetrabutyl ammonium borohydride and stirred for about 50 min. The reaction mixture was then quenched with saturated NaHCO$_3$ solution, diluted with water, and extracted (2 ×) with CH$_2$Cl$_2$. The combined organic portions were washed with brine, dried over anhydrous Na$_2$SO$_4$, filtered, and concentrated in vacuo. Column chromatography (silica gel, 10% hexane/90% ethyl acetate to 100% ethyl acetate) provided 288 mg (77%) of the title compound as a white solid. Analysis showed the crude product to exist in a 8:92 cis:trans ratio.

m.p. =164°–166°

NMR: MHz (DMSO-d$_6$): δ 1.20 (d, 3H J=6 Hz); 3.53–3.56 (M, 1H); 4.33–4.37 (M, 1H); 4.46 (S, 2H); 6.90–7.28 (M, 5H); 8.11 (S, 1H); 8.75 (d, 1H, J=9 Hz)

IR (KBr) 3280, 2915, 1759.4, 1658.3, 1546.7, 1499, 1254 cm$^{-1}$

MS (FAB) m/e=235 (M +1)

UV (ethanol) λ=275 nm (ε=1060); λ=269 nm (ε=1270)

OR (DMSO) −57.49° at 589 nm; −174.22° at 365 nm

Elem. Anal. calc'd: C:61.53 H:6.02 N:11.96; obs'd: C:61.35 H:5.97 N:11.80

EXAMPLE 13

3-β-Phenoxyaoetylamino-4-β-(3-chloro-2-hydroxy-prop-1-yl)azetidin-2-one

A. Alkylation

In a procedure analogous to that of Example 11, 3-β-phenoxyacetylamino-4-β-phenylsulfonyl-1-t-butyl-dimethylsilyl-azetidin-2-one was alkylated with 1-chloro-2,3-epoxypropane to provide 3-β-phenoxyacetylamino-4-β-phenylsulfonyl-4-(3-chloro-2-hydroxy-prop-1-yl)-1-t-butyldimethylsilyl-azetidin-2-one in 20% yield.

m.p. (dec.) = >165°

NMR 300 MHz (CDCl$_3$): 0.36 (S, 3H); 0.39 (S, 3H); 0.89–0.99 (M, 1H) 1.07 (S, 9H); 2.24–2.29 (M, 1H); 2.52–2.59 (M, 1H); 2.84 (S, 1H); 3.07–3.12 (M, 1H); 4.80–4.90 (M, 1H); 4.20 and 4.51 (ABq, 2H, J=15 Hz); 6.31 (d, 1H, J=12 Hz); 6.39–7.05 (M, 5H); 7.62–8.01 (M, 5H); 8.44 (d, 1H, J=9 Hz)

IR (KBr): 3281, 1768.5, 1661, 1309, 1210.5, 1155 cm$^{-1}$

MS (FAB) m/e=567 (M +), 425 (—SO$_2$ phenyl)

UV (ethanol) λ=218 nm (ε=14900); λ=268 nm (ε=1920); λ=274 nm (ε=1630)

OR (DMSO) +42.59° at 589 nm; +198.15° at 365 nm

Elem. Anal. calc'd: C:55.06 H:6.22 N:4.95; obs'd: C:54.86 H:6.18 N:4.89

B. Deprotection

In a procedure analogous to that of Example 12, 3-β-phenoxyacetylamino-4-α-phenylsulfonyl-4-(3-chloro-2-hydroxy-prop-1-yl)-1-t-butyldimethylsilylazetidin-2-one was converted to 3-β-phenoxyacetylamino-4-α-phenylsulfonyl-4-(3-chloro-2-hydroxy-prop-1-yl)-azetidin-2-one in 75% yield.

m.p. (dec.) >95° C.

300 MHz (CDCl$_3$) δ 1.43–1.52 (M, 1H); 2.26 (d, 1H, J=15 Hz); 2.92–2.99 (M, 1H); 3.22–3.27 (M, 1H); 3.65 (S, 1H); 4.03–4.05 (M, 1H); 4.41 and 4.53 (ABq, 2M, J=15 Hz); 5.87 (d, 1H, J=9 Hz); 6.69–7.20 (M, 5H); 7.39 (S, 1H); 7.62–8.03 (M, 5H); 8.41 (d, 1H, J=9 Hz)

IR (KBr) 3327, 1791, 1675, 1523, 1495, 1306, 1151 cm$^{-1}$

MS (FAB) m/e=452 (M-1), 311 (—SOH$_2$ phenyl)

UV (ethanol) λ=216 nm (ε17,400); λ=268 nm (ε=2500); λ=275 nm (ε=2200)

OR (DMSO) +15.59° at 589 nm +68.23° at 365 nm

Elem. Anal. calc'd: C:53.04 H:4.67 N:6.19 ; obs'd: C:54.86 H:6.18 N:4.89

C. Reduction

In a procedure analogous to that of Example 11, 3-β-phenoxyacetylamino-4-α-phenylsulfonyl-4-β-(3-chloro-2-hydroxy-prop-1-yl)-azetidin-2-one was converted to 3-β-phenoxyacetylamino-4-β-(3-chloro-2-hydroxy-prop-1-yl)-azetidin-2-one in 45% yield.

m.p. (dec.) 135°–140° C.

NMR 300 MHz (DMSO-d$_6$): δ 1.49–1.68 (M, 2H); 3.36–3.47 (M, 2H); 3.52–3.59 (M, 1H); 3.73–3.79 (m, 1H); 4.50 (S, 2H); 5.03–5.07 (M, 1H); 5.19 (d, 1H, J=6 Hz); 6.88–7.27 (M, 5H); 8.15 (S, 1H); 8.87 (d, 1H, J=9 Hz)

IR (KBr) 3457, 3355, 1756, 1735, 1163, 1536, 1497, 1214, 1062 cm$^{-1}$

MS (FAB) m/e=313 (M +)

UV (ethanol) λ=269 (ε=1500) λ=275 (ε=1270)

OR (DMSO): +27.73° at 589 nm; +105.36° at 365 nm
Elem. Anal. calc'd: C:53.77 H:5.48 N:8.96 ; obs'd: C:53.51 H:5.41 H:8.73

EXAMPLE 14

3-β-Phenoxyacetylamino-4-β-(2-fluoroeth-1-yl)-azetidin-2-one

A. Alkylation

In a manner analogous to the foregoing examples, 1-t-butyldimethylsilyl-3-β-phenoxyacetylamino-4-α-phenylsulfonyl-azetidin-2-one was alkylated with. 1-bromo-2-fluoroethane.
m.p. (dec.) 158°–159° C.
NMR 300 MHz (CDCl$_3$): δ 0.36 (S, 3H); 0.44 (S, 3H); 1.09 (S,9H); 1.55–1.64 (M, 1 Hz); 2.22–2.43 (M, 1H); 4.28 and 4.47 (ABq, 2H, J=15 Hz) 4.33–4.70 (M, 2H); 6.30 (d, 1H, J=12 Hz); 6.58–7.14 (M, 5H); 7.58–8.02 (M, 5H)
IR (KBr); 3408, 1761, 1700, 1533, 1497, 1310, 1266, 1233, 1150 cm$^{-1}$
MS (FAB) m/e =521, 379 (—SO$_2$ phenyl)
UV (ethanol) λ=217 nm (ε=17500); λ=268 nm (ε=2270); λ=274 nm (ε=1870)
OR (DMSO) +29.23° at 589 nm; +119.00° at 365 nm

B. Deprotection m.p. (dec.) 152°–154° C.
NMR 300 MHz (CDCl$_3$): δ 1.97–2.12 (M, 1H); 2.24–2.44 (M, 1H); 4.50 (S, 2H); 4.55–4.69 (M, 1H); 4.78–4.87 (M, 1H); 5.72 (d, 1H, J=12 Hz) 6.78–7.25 (M, 5H); 6.87 (S, 1H); 7.43–7.78 (M, 5H); 8.05 (d, 1M J=9H)
IR (KBr) 3300, 1771, 1674, 1532, 1496, 1332, 1310, 1226, 1151 cm$^1$
MS (FAB) m/e=407 (M+), 265 (—SO$_2$ phenyl)
UV (ethanol) λ=216 nm (ε=17800); λ=268 nm (ε=2300) λ=275 nm (ε=2030)
OR (DMSO): +12.02° at 589 nm; +66.13° at 365 nm
Elem. Anal. calc'd: C:56.15 H:4.71 N:6.89; obs'd: C:56.39 H:4.83 N:7.02

C. Reduction (ratio of cis/trans 91:9)
m.p. (dec.) 180°–182° C.
NMR 300 MHz (DMSO-d$_6$): δ 1.65–1.80 (M, 2H); 3.69–3.73 (M, 1H); 4.29–4.33 (M, 1H); 4.44–4.48 (M, 1H); 4.52 (S, 2H); 5.06–5.11 (M, 1H); 6.88–7.27 (M, 5H); 8.35 (S, 1H); 8.86 (d, 1H, J=9 Hz)
IR (KBr) 3268, 3262, 3082, 1771, 1731, 1669, 1557, 1223, 1027 cm$^{-1}$
MS (FD) m/e=266 (M+)
UV (ethanol) λ=269 nm (ε=1310); λ=275 nm (ε=1070)
OR (DMSO): +75.85° at 589 nm; +231.54° at 365 nm
Elem. Anal. calc'd: C:58.64 H:5.68 N:10.51 obs'd: C:58:82 H:5.78 N:10.60

EXAMPLE 15

3-β-Phenoxyacetylamino-4-β-(2-hydroxyeth-1-yl)-azetidin-2-one

A. Alkylation

In a manner analogous to the foregoing examples, 1-t-butyldimethylsilyl-3-β-phenoxyacetylamino-4-α-phenylsulfonyl azetidin-2-one was alkylated with ethylene oxide to provide 1-t-butyldimethylsilyl-3-β-phenoxyacetylamino-4-α-phenylsulfonyl-4-β-(2-hydroxyeth-1-yl)-azetidin-2-one.
m.p. =143°–146° C.
NMR 300 MHz (CDCl$_3$): δ 0.36 (S, 3H); 0.42 (S, 3H); 1.08 (S, 9H); 1.24–1.40 (M, 1H); 2.03–2.25 (M, 2H); 3.61–3.82 (M, 2H); 4.22 and 4.39 (ABq, 2H, J=15 Hz); 6.32 (d, 1H, J=12 Hz); 6.52–7.10 (M, 5H); 7.56–8.00 (M, 5H); 8.64 (d, 1H, J=12 Hz)
IR (KBr) 3518, 2940, 1754, 1692, 1303, 1264, 1212, 1150 cm$^{-1}$
MS m/e=519 (M+)
UV (ethanol) δ=217 nm (ε=16400); λ=268 nm (ε=2030); λ=274 nm (ε=1700)
OR (DMSO): +56.93° at 589 nm +235.29° at 365 nm
Elem. Anal. calc'd: C:57.89 H:6.61 N:5.40 obs'd: C:57.81 H:6.50 N:5.65

B. Deprotection m.p.(dec.)>90° C.
300 MHz (CDCl$_3$): δ 1.70–1.80 (M, 1H); 2.16 (d, 1H, J=15 Hz); 2.76 (S, 1H); 3.69–3.90 (M, 2H); 4.42 and 4.49 (Abq, 2H, J=15 Hz); 5.91 (d, 1H, J=12 Hz); 6.72–7.19 (M, 5H); 7.36 (S, 1H) 7.59–8.01 (M, 5H); 8.56 (d, 1H, J=12 Hz)
IR (KBr) 3296, 3202, 1787, 1672, 1527, 1495, 1305, 1239, 1151, 1071 cm$^{-1}$
MS (FAB) m/e=405 (M+), 263 (—SO$_2$ phenyl)
UV (ethanol) λ=218 nm (ε=16500); λ=268 nm (ε=2120); λ=274 nm (ε=1780)
OR (DMSO) +19.69° at 589 nm; +74.80° at 365 nm
Elem. Anal. calc'd: C:56.42 H:4.98 N:6.92 ; obs'd: C:56.06 H:5.14 H:6.73

C. Reduction m.p. (dec.)>185° C.
NMR 300 MHz (DMSO-d$_6$): δ 1.45–1.53 (M, 2H); 3.31–3.35 (M, 2H); 3.67–3.73 (M, 1H); 4.46–4.50 (S, 3H); 5.01–5.06 (M, 1H); 6.88–7.27 (M, 5H); 8.25 (S, 1H); 8.84 (d, 1H, J=9 Hz)
IR (KBr): 3269, 1754, 1715, 1673, 1558, 1496, 1222 cm$^{-1}$
MS (FAB) m/e=265 (M+1)
UV (ethanol) λ=268 nm (ε=1420); λ=275 nm (ε=1170)
OR (DMSO): +56.20° at 589 nm; +203.49 ° at 365 nm
Elem. Anal. calc'd: C:59.08 H:6.10 N:10.60; obs'd: C:58.61 H:6.02 N:10.15

EXAMPLE 16

7-β-Phenoxyacetylamino-4-methylazetidin-2-one

A. Alkylation

A sample of 7-β-phenoxyacetylamino-4-β-phenylsulfonyl-1-t-butyldimethylsilyl-azetidin-2-one is alkylated using n-butyllithium and methyl iodide.

B. Electrolytic Reduction and Deprotection

The cathode compartment was fitted with a mercury ring cathode and a magnetic stirring bar. The cathode compartment was then charged with 55 ml of a 0.1 molar solution of tetrabutylammonium hydrogen sulfate dissolved in dimethylformamide. The solution was kept at a constant temperature of about 25° C. by means of a circulating refrigerated bath. Dissolved in the cathode was 283.8 mg of 3-β-phenoxyacetylamino-4-α-phenylsulfonyl-4-β-methyl-l-t-butyldimethylsilylazetidin-2-one.

The anode compartment was fitted with a platinum wire anode, an anolyte presoaked Nafion ® 425 cation exchange membrane, and charged with a 0.25 molar solution of pH 2.7 sodium phosphate buffer. The anode compartment was then positioned within the cathode compartment. The anode compartment was charged with sufficient anolyte such that thè level of the anolyte was approximately the same as the level of the catholyte. At this point, the catholyte was deoxygenated using a stream of inert gas and bubbler. The electrodes were then attached to the appropriate terminals of a potentiostat and a controlled potential of —2.2 V (vs.S.C.E.) was applied. The reaction proceeded at this potential until complete as determined by TLC.

The catholyte solution was rotoevaporated to near dryness and applied to a liquid chromatography column (5 cm dia. filled to 15 cm with Kiesegel 60; flow rate =40 ml/min.; eluent =acetone; pressure =7 psi). The appropriate chromatography fractions were reduced in volume under vacuum to produce 114.2 mg of the desired product. The product was produced at 51 percent current efficiency and recovered at 84 percent (cis and trans) of theoretical yield.

NMR of cis product (270 MHz; DMSOd6): d, 1.03; m, 377; s, 4.57; dd, 5.04; m, 6.97; m, 7.32; m, 8.50.

We claim:

1. A process for preparing compounds of Formula (I)

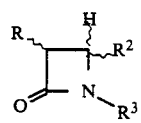

wherein R is a protected amino group; hydroxy ($C_1$-$C_4$) alkyl, protected hydroxy ($C_1$-$C_4$) alkyl, $C_2$-$C_4$ alkenyl, $C_1$-$C_4$ alkyl or hydrogen; $R^2$ is $C_1$-$C_{12}$ alkyl, $C_1$-$C_{12}$ substituted alkyl, $C_2$-$C_6$ alkenyl, $C_2$-$C_6$ substituted alkenyl, $C_2$-$C_6$ alkynyl, $C_2$-$C_6$ substituted alkynyl; and $R^3$ is an amide-protecting group, $C_2$-$C_6$ alkenyl, $C_2$-$C_6$ alkynyl, or hydrogen; which comprises (a) reaction of a compound of Formula (II):

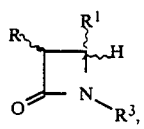

wherein $R^1$ is triphenylphosphonium, —$SO_2R'$, CN, or

wherein $R'$ is $C_1$-$C_6$ alkyl, phenyl, substituted phenyl, phenyl $C_1$-$C_6$ alkyl, or $C_1$-$C_6$ substituted alkyl; and R and $R^3$ have the same meanings as defined for Formula (I); with strong base in the presence of a compound of the formula $R^2$-L, wherein L is a leaving group; and $R^2$ has the same meanings as defined for Formula (I); followed by (b) reduction with a hydride reducing agent or reduction under dissolving metal conditions.

2. The process of claim 1 wherein $R^1$ is —$SO_2R'$.

3. The process of claim 2 wherein $R^1$ is —$SO_2R'$ and $R'$ is phenyl.

4. A process for preparing compounds of Formula (I)

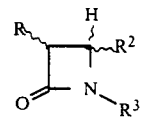

wherein R is a protected amino group, hydroxy ($C_1$-$C_4$)-alkyl, protected hydroxy ($C_1$-$C_4$) alkyl, hydrogen, $C_2$-$C_4$ alkenyl, or $C_1$-$C_4$ alkyl; $R^1$ is triphenylphosphonium, —$SO_2R'$, CN, or

wherein $R'$ is $C_1$-$C_6$ alkyl, phenyl, substituted phenyl, phenyl $C_1$-$C_6$ alkyl, or $C_1$-$C_6$ substituted alkyl; $R^2$ is $C_1$-$C_{12}$ alkyl, $C_1$-$C_{12}$ substituted alkyl, $C_2$-$C_6$ alkenyl, $C_2$-$C_6$ substituted alkenyl, $C_2$-$C_6$ alkynyl, or $C_2$-$C_6$ substituted alkynyl; and $R^3$ is an amide-protecting group, $C_2$-$C_6$ alkenyl, $C_2$-$C_6$ alkynyl, or hydrogen which comprises subjecting a compound of Formula (III)

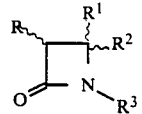

(a) to dissolving metal reduction; or (b) reduction with a hydride reducing agent.

5. The process of claim 1 wherein step (b) is a dissolving metal reduction.

6. The process of claim 1 wherein step (b) is a reaction with a hydride reducing agent.

7. The process of claim 6 wherein $R^1$ is —$SO_2R'$.

8. The process of claim 7 wherein $R^1$ is —$SO_2R'$ and $R'$ is phenyl.

9. The process of claim 8 wherein the hydride reducing agent is selected from a list consisting of $NaBH_4$, $NaCNBH_3$,

$Zn(BH_4)_2$, $LiAlH(O—C(CH_3)_3)_3$, n—$Bu_4NBH_4$, $KB[CH(CH_3)C_2H_5]_3H$, $LiCNBH_3$, $LiAlH_4$, $[(CH_3OCH_2CH_2O)_2AlH_2]$-Na, $LiB(CH_3CH_2)_3H$, $(CH_3)_4NBH_4$, diborane, $Na(CH_3O)_3BH$, lithium trisiamylborohydride, diisobutylaluminium hydride, potassium trisiamylborohydride, $Ca(BH_4)_2$, or $NaBH_4$—$CeCl_3$.

10. The process of claim 9 wherein the hydride reducing agent is $LiAl_3H$.

11. The process of claim 9 wherein the hydride reducing agent is tetra-n-butyl ammonium borohydride.

12. The process of claim 4 wherein the hydride reducing agent is selected from a group consisting of $NaBH_4$, $NaCNBH_3$,

Zn(BH₄)₂, LiAlH (O-C(CH₃)₃)₃, n-Bu₄NBH₄, KB₃H, LiCNBH₃, LiAlH₄-Na, LiB(CH₃CH₂)₃H, (CH₃)₄NBH₄, diborane, Na(CH₃O)₃BH, lithium trisiamylborohydride, diisobutylaluminium hydride, potassium trisiamylborohydride, Ca(BH₄)₂, or NaBH₄—CeCl₃.

13. The process of claim 12 wherein the hydride reducing agent is tetra-n-butylammonium borohydride.

14. The process of claim 12 wherein the hydride reducing agent is LiAl(Ot-butyl)₃H.

15. The process of claim 14 wherein R² is 4-butene-1-yl and R' is phenylsulfonyl.

16. A process for preparing compounds of Formula (III)

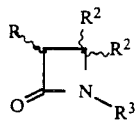 (III)

wherein R is a protected amino group; hydroxy (C₁–C₄) alkyl, protected hydroxy (C₁–C₄) alkyl, C₂–C₄ alkenyl, C₁–C₄ alkyl, or hydrogen; R¹ is triphenylphosphonium, —SO₂R', CN, or

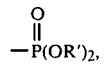

wherein R' is C₁–C₆ alkyl, phenyl, substituted phenyl, phenyl C₁–C₆ alkyl, or C₁–C₆ substituted alkyl; R² is C₁–C₁₂ substituted alkyl, C₂–C₆ alkenyl, C₂–C₆ substituted alkenyl, C₂–C₆ alkynyl, C₂–C₆ substituted alkynyl; and R³ is an amide-protecting group, C₂–C₆ alkenyl, C₂–C₆ alkynyl, or hydrogen which comprises:

reaction of a compound of Formula (II):

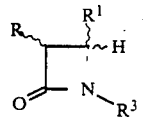

with strong base in the presence of a compound of the formula R²-L, wherein L is a leaving group.

17. The process of claim 16 wherein R¹ is —SO₂R'.

18. The process of claim 17 wherein R² is C₂–C₆ alkenyl or C₁–C₁₂ alkyl.

19. The process of claim 18 wherein R¹ is phenylsulfonyl and R² is 4-butene-1-yl.

* * * * *

UNITED STATES PATENT AND TRADEMARK OFFICE
CERTIFICATE OF CORRECTION

PATENT NO. : 4,992,545
DATED : February 12, 1991
INVENTOR(S) : Hall, deceased et al.

It is certified that error appears in the above-identified patent and that said Letters Patent is hereby corrected as shown below:

Claim 10, column 22, line 63, delete "$LiAl_3H$" should read --$LiAlH(O-C(CH_3)_3)_3$--.

Claim 12, column 23, line 6, "$KB_3H$" should read --$KB(CH(CH_3)C_2H_5)_3H$--.
   column 23, line 7, "$LiAlH_4$-Na" should read --$LiAlH_4$, $((CH_3OCH_2CH_2O)_2AlH_2)$-Na--.

Claim 16, column 23, Formula (III), lines 20-25, one of the two "$R^2$" should be --$R^1$--.

Signed and Sealed this

Fifteenth Day of September, 1992

Attest:

DOUGLAS B. COMER

Attesting Officer    Acting Commissioner of Patents and Trademarks